(12) United States Patent
Glad et al.

(10) Patent No.: US 7,122,381 B2
(45) Date of Patent: Oct. 17, 2006

(54) SELECTIVE AFFINITY MATERIAL, PREPARATION THEREOF BY MOLECULAR IMPRINTING, AND USE OF THE SAME

(76) Inventors: Magnus Glad, Nyckelkroken 64, SE-222 47 Lund (SE); Maria Kempe, Knut den Stores gata 1 C, SE-222 21 Lund (SE); Klaus Mosbach, Lackalänga 31, SE-244 94 Furulund (SE)

( * ) Notice: Subject to any disclaimer, the term of this patent is extended or adjusted under 35 U.S.C. 154(b) by 12 days.

(21) Appl. No.: 08/199,300

(22) PCT Filed: Sep. 4, 1992

(86) PCT No.: PCT/SE92/00610
§ 371 (c)(1),
(2), (4) Date: May 5, 1994

(87) PCT Pub. No.: WO93/05068
PCT Pub. Date: Mar. 18, 1993

(65) Prior Publication Data
US 2003/0049870 A1 Mar. 13, 2003

(30) Foreign Application Priority Data
Sep. 6, 1991 (SE) .............................. 9102622

(51) Int. Cl.
*G01N 33/543* (2006.01)
*G01N 33/553* (2006.01)
*G01N 33/552* (2006.01)
*G01N 33/545* (2006.01)
*C12Q 1/00* (2006.01)

(52) U.S. Cl. ............... 436/518; 435/4; 435/6; 435/7.1; 435/174; 435/180; 435/181; 436/525; 436/527; 436/529; 436/530; 436/531

(58) Field of Classification Search ............. 435/4, 435/6, 7.1, 174, 181, 283.1, 287.1, 287.6, 435/287.7, 287.8; 436/518, 525, 527, 529, 436/530, 531
See application file for complete search history.

(56) References Cited

U.S. PATENT DOCUMENTS

| 4,269,605 A | | 5/1981 | Dean et al. ............... 23/230 B |
| 5,110,833 A | * | 5/1992 | Mosbach .................... 521/50 |

(Continued)

FOREIGN PATENT DOCUMENTS

| DE | 2 358 647 | 11/1973 |
| EP | 0 364 772 | 9/1989 |

(Continued)

OTHER PUBLICATIONS

Ekberg et al. 1989. TIBTECH. vol. 7: 92–96.*
Figueroa et al. 1986. J. of Chromatography. 371: 335–352.*
Glad et al. 1985. J. of Chromatography. 347: 14–23.*

(Continued)

*Primary Examiner*—Nita Mannifield
*Assistant Examiner*—J. Hines
(74) *Attorney, Agent, or Firm*—Morgan & Finnegan, L.L.P.

(57) ABSTRACT

A selective adsorption material made by the process comprising: a) non-cavalently or reversibly-covalently binding a print molecule to at least two styrene, acrylate or silica monomers, each of which monomers brinds to said print molecule by means of a different functional group; b) immobilizing said bound monomers by being polymerized to each other in the presence of an effective amount of cross-linker; and c) removing said print molecule from said polymer by extraction to leave a cavity in said polymer which is stereo-tailored to a biological molecule of interest; and wherein said print molecule is the biological molecule of interest.

22 Claims, 2 Drawing Sheets

U.S. PATENT DOCUMENTS

| | | | | |
|---|---|---|---|---|
| 5,310,648 | A | * 5/1994 | Arnold et al. | 435/5 |
| 5,372,719 | A | * 12/1994 | Afeyan et al. | 210/502.1 |
| 5,453,199 | A | 9/1995 | Afeyan et al. | 210/638 |

FOREIGN PATENT DOCUMENTS

| | | |
|---|---|---|
| EP | 0 552 630 | 1/1993 |
| GB | 1133328 | 2/1966 |
| JP | 60 181155 | 9/1985 |
| JP | 6-323949 | 11/1994 |
| SE | 8404967 | 4/1986 |
| WO | WO 90/07527 | 7/1990 |
| WO | WO 02/19663 | 11/1992 |
| WO | WO 94/11403 | 5/1994 |
| WO | WO 94/14835 | 7/1994 |

OTHER PUBLICATIONS

O. Ramström et al., "Recognition Situ Incorporating Both Pyridinyl and Carboxy Functionalities Prepared by Molecules Inprinting," J. Org. Chem. 1993, 58, 7562–7564.*

"Molecular Imprinting: A Technique for Producing Specific Separation Materials", TIBTECH, vol. 7, Apr. 1989, Björn Ekberg et al.

"Use of Silane Monomers for Molecular Imprinting and Enzyme Entrapment in Polysiloxane–Coated Porous Silica", Journal of Chromatography, vol. 347, 1985, pp. 11–23, Magnus Glad, et al.

"Synthesis of Substrate–Selective Polymers by Host–Guest Polymerization", Makromol. Chem. 182, 687–692, (1981), Reza Arshady et al.

"Imprinting Of Amino Acid Derivatives in Macroporous Polymers", Lars Andersson et al., Tetrahedron Letters, vol. 25, No. 45, pp. 5211–5214, 1984.

"Polymeric Reagents and Catalyts", ACS Symposium Series, Developed from a symposium sponsored by the Divisions of Organic and Polymer Chemistry at the American Chemical Society, Miami Beach, Florida, Apr. 28–May 3, 1985, pp. 186–230. Günter Wulff.

"Improved Chromatography: Prearranged Distances Between Boronate Groups by the Molecular Imprinting Approach", Olof Norrlöw et al., Journal of Chromatography, 396 (1987) 374–377, Elsevier Science Publishers B.V. Amsterdam.

"Synthesis of Cellulosse Derivatives Containing the Dihydroxyboryl Group and a Study of Their Capacity to Form Specific Complexes with Sugars and Nucleic Acid Components", H.L. Weith et al., Biochemistry, vol. 9, No. 22, 1970, pp. 4396–4401.

"The Interaction of Chain Molecules Carrying Reactive and Catalytic Chain Substituents", H. Morawetz and W.R. Song, Journal of the American Chemical Society, 88:24, Dec. 20, 1966, pp. 5714–5718.

High–Performance Immobilized–Metal Affinity Chromatography of Proteins on Iminodiacetic Acid Silica–Based Bonded Phases, Alvaro Figueroa et al., Journal of Chromatography, 371, (1986) 335–377, Elsevier Science Publishers B.V. Amsterdam.

"The Synthesis of a D–Amino Acid Ester in an Organic Media With a α–Chymotryspin Modified by a Bio–Imprinting Procedure", Marianne Ståhl et al., Biotechnology Letters, vol. 12, No. 3, pp. 161–166 (1990).

"Protein Separation and Purification in Neat Dimethyl Sulfoxide", Nancy Chang et al., Biochemical and Biophysical Research Communications, vol. 176, No. 3, (1991) May 15, 1991, pp. 1462–1468.

"Preparation and Properties of Porous Particles from Trimethylolpropane Trimethacrylate", Per Reinholdsson et al., Die Angewandte Makromolekulare Chemie 192, (1991), pp. 113–132.

"Synthesis of Some and Amino Acid Derivatives of Styrene", L.R. Morris et al., JACS, 81, (1959), pp. 377–382.

"Metal Chelate Affinity Chromatography, A New Approach to Protein Fractionation", Jerker Porath et al., Nature, vol. 258, Dec. 18, 1975, pp. 598–599.

Lars Andersson, et al.; "Enantiomeric Resolution On Molecularly Imprinted Polymers Prepared With Only Non Covalent And Non–Ionic Interactions"; Journal of Chromatography: 516 (1990); pp. 313–322.

Andersson Li et al, Dialog Information Services, File 154, Medline, Dialog accession No. 07658968, Medline accession No. 91177968, J. Chromatogr. Sep. 21, 1990, 516(2): p. 323–331 (Abstract).

Andersson et al, Plennum Press, "Bioseparation and Catalysis in Molecularly Imprinted Polymers"; "Molecular Interactions in Bioseparations" (Ngo. T.T. ed.), 383–394.

Lars Andersson, et al; "Molecular Recognition In Synthetic Polymers: Preparation Of Chiral Stationary Phases By Molecular Imprinting Of Amino Acid Amides"; J. Chromatography; 513 (1990); pp. 167–179.

Braun et al, 108 Chemiker–Zeitung, 255–257 "Ionenselektive Austauscherharze durch vernetzende Copolymerisation vinylsubtituierter Metallkomplexe" (1984).

Styrbjörn Byström, et al.; "Selective Reduction Of Steroid 3– And 17–Ketones Using LiAlH$_4$ Activated Template Polymers"; J. Am. Chem. Soc.; Mar. 10, 1993; 115; pp. 2081–2083.

Wayne Danen, et al.; "Stereoselective Synthesis Via A Photochemical Template Effect"; J. American Chemical Society; Apr. 23, 1980; 102:9; pp. 3265–3267.

Julien Damen et al., "Stereoselective Syntheses . Via a Photochemical Template Effect", Journal of the American Chemical Society, vol. 102, No. 9, Apr. 1980, pp. 3265–3267.

Bjorn Ekberg and Klaus Mosbach: "Molecular imprinting: a technique for producing specific separation materials", TIBTECH, vol. 7, 1989, pp. 92–96.

Lutz Fischer, et al.; "Direct Enantioseparation of β–Adrenergic Blockers Using A Chiral Stationary Phase Prepared By Molecular Imprinting"; J. Am. Chem. Soc., 1991, 113, 9358–9360.

Magnus Glad et al: "Use of silane monomers for molecular imprinting and enzyme entrapment in polysiloxane–coated porous silica", Journal of Chromatography, vol. 347, 1985, pp. 11–23, see especially pp. 20–21.

Hedborg E. et al., "Some studies of molecularly–imprinted polymer membranes in combination with field–effect devices" Dialog Information Services, File 34, Scisearch, Dialog accession No. 12613654, Sensors and Actuators A–physical, 1993, V37–8,jun–(Jun.–Aug.), p. 796–799 (Abstract).

Kempe, et al, "Chiral recognition of N. alpha protected amino acids and derivatives in non–covalently molecularly imprinted polymers", Int. J. Pept. Protein Res. (1994), 44(6), 603–6, pp. 4–6.

Kempe et al, "Direct resolution of naproxen on a non–covalently molecularly imprinted chiral stationary phase" 664 J. Chromatogr., 276–279 (1994).

Kempe M et al, "Binding Studies on Substrate– And Enantio–Selective Molecularly Imprinted Polymers" Dialog Information Services, File 34, Scisearch, Dialog accession No. 10998079; Analytical Letters, 1991, V24, N7, P1137–1145 (abstract).

Mayes, et al; "Sugar Binding Polymers Showing High Anomeric And Epimeric Discrimination Obtained By Non-covalent Molecular Imprinting"; Analytical Biochemistry; vol. 222, No. 2, Nov. 1, 1994; pp. 483–488.

Klaus Mosbach, "Enzymes Bound to Artificial Matrixes", Scientific America, Mar. 1971, pp. 26–33.

Ann–Christin Johansson and Klaus Mosbach, "Acrylic Copolymers As Matrices for the Immobilization of Enzymes" Biochimica et Diophysica Acta, Jun. 10, 1974, pp. 339–347.

H. Nilsson, R. Mosbach, and K. Mosbach, "The Use of Bead Polymerization of Acrylin Monomers for Immobilization of Enzymes", Biochimica et Biophysica Acta, Feb. 18. 1972, pp. 253–256.

Mosbach, K., "Molecular imprinting" Trends in Biochemical Sciences 19, (Jan. 1994) pp. 9–14.

Kurt G.I. Nilsson, "Enzymatic Synthesis of Oligosaccharides", TIBTECH, Oct. 1988, vol. 6, pp. 256–264.

Olof Norrlow, et al.; "Acrylic Polymer Preparations Containing Recognition Sites Obtained By Imprinting With Substrates"; J. Of Chromatography; 229 (1984); pp. 29–41.

O'Shannessy DJ et al., "Molecular Recognition in Synthetic Polymers" National Library of Medicine, File Medline, NLM accession No. 90267842, J. Mol. Recognit. Jul. 1989; 2(1):1–5 (Abstract).

Daniel J. O'Shannessy et al, "Recent Advances in the Preparation and use of Molecularly Imprinted Polymers for Enantiomeric Resolution of Amino Acid Derivatives", Journal of Chromotography, vol. 470, 1989, pp. 391–399.

Anthony Paine; "Dispersion Polymerization Of Styrene In Polar Solvents. IV. Solvency Control Of Particle Size From Hydroxypropyl Cellulose Stabilized Polymerizations"; J. Polymer Science; vol. 28; No. 9; Aug. 1990; pp. 2485–2500.

Z. Pelzbauer, et al.; "Reactive Polymers"; J. Of Chromatography; 171 (1979); pp. 101–107.

Olof Ramstrom, et al.; "Synthetic Peptide Receptor Mimics: Highly Stereoselective Recognition In Non–Covalent Molecularly Imprinted Polymers"; Tetrahedron:Asymmetry, vol. 5; No. 4; Apr. 1994; pp. 649–656.

Olof Ramstrom, et al.; "Recognition Sites Incorporating Both Pyridinyl And Carboxy Functionalities Prepared By Molecular Imprinting"; J. Org. Chem.,; vol. 58; Dec. 17, 1993; No. 26; pp. 7562–7564.

Per Reinholdsson, et al.; "Preparation And Properties Of Porous Particles From Trimethylolpropane Trimethacrylate"; Applied Macromolecular Chemistry And Physics; 192 (1991); pp. 113–132.

Manfred Munzer, et al.; "Polymerization Process"; John Wiley & Sons; 1977; pp. 106–143.

Andrea Schmid, et al.; "Porosity Determination Of Poly(trimethylolpropane Trimethacrylate) Gels"; Macromolecul. Chem.; vol. 192; No. 5; May 1991; pp. 1223–1235.

Sellergren, B., "Imprinted dispersion polymers: a new class of easily accessible affinity stationary phases", 673 J. Chromatogr., 133–141 (1994).

Borje Sellergren; "Direct Drug Determination By Selective Sample Enrichment On An Imprinted Polymer"; Anal. Chem.; May 1, 1994; vol. 66; pp. 1578–1582.

A. Guyot; "Syntheses And Separations Using Functional Polymers"; John Wiley & Sons; 1988; pp. 1–43.

Vlatakis et al., "Drug assay using antibody mimics made by molecular imprinting" Nature (993) 61: pp. 645–647.

B. Williamson, et al.; "The Preparation Of Micron–Size Polymer Particles In Nonpolar Media"; J. Colloid And Interface Science; vol. 119; 1987; pp. 559–564.

Günter Wülff et al., Abstract No. 36407h, "Enzyme–Analog Built Polymers. 26. Enantioselective Synthesis of Amino Acids Using Polymers Possessing Chiral Cavities Obtained by Imprinting Procedure With Template Molecules", Chemical Abstracts, vol. 112, No. 5, Jan. 29, 1990, (Columbus, Ohio, USA), Makromol. Chem. 1989, 190(7), pp. 1727–1735.

Günter Wülff, et al.; "Racemic Resolution Of Free Sugars With Macroporous Polymers Prepared By Molecular Imprinting Selectivity Dependence On The Arrangement Of Functional Groups Versus Spatial Requirements"; J. Org. Chem.; vol. 56; Jan. 4, 1991; No. 1; pp. 395–400.

Günter Wülff, et al.; "Influence Of The Nature Of The Crosslinking Agent On The Performance Of Imprinted Polymers In Racemic Resolution"; Makromol. Chem.; 188 (1987); pp. 731–740.

Günter Wülff, et al; "The Role Of Binding–Site Interactions In The Molecular Imprinting Of Polymers"; Trends In Biotechnology; Mar. 1993; vol. 11; 85–87.

Günter Wülff, et al.; Enzyme–Analogue Built Polymers, 18 Chiral Cavities in Polymer Layers Coated on Wide–Pore Silica; Reactive Polymers 3, (1985) pp. 261–275.

Günter Wülff, et al.; "Enantioselective Synthesis of Amino Acids Using Polymers Possessing Chiral Cavities Obtained by an Imprinting Procedure With Template Molecules"; Enzyme–Analogue Built Polymers, 26, , Makromol Chem., (1989), vol. 190(7), pp. 1727–1735.

* cited by examiner

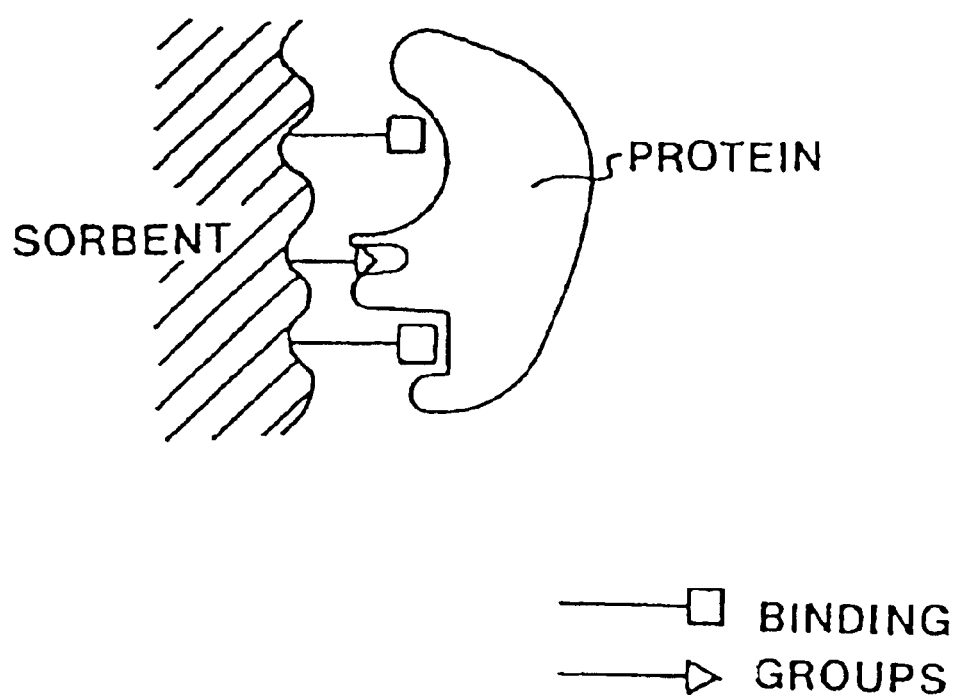

SELECTIVE AFFINITY MATERIAL, PREPARATION THEREOF BY MOLECULAR IMPRINTING, AND USE OF THE SAME

FIELD OF THE INVENTION

The invention relates to a selective adsorption material, especially suitable for adsorption of biological macromolecules, a process for preparing this selective adsorption material, and the use thereof for purification and analysis, especially of biological macromolecules.

BACKGROUND OF THE INVENTION

It Is known to prepare homogeneous gels while using the so-called molecular imprinting technique by making imprints of dyes (R. Arshady, K. Mosbach; Makromol. Chemie, 182 (1981) 687) and amino acid derivatives (L. Andersson, B. Sellergren, K. Mosbach, Tetrahedron Lett. 25 (1984) 5211). Merely non-covalent bonding between a "print molecule" and monomers is used. After polymerisation of the monomers and removal of the print molecule, a selective polymer is obtained, based on binding groups correctly immobilised in space and present in cavities which have the shape of a mould of the print molecule. A summary of this technique is given by B. Ekberg, K. Mosbach, in Trends Biotechnol., 7 (1989) 92.

It is known to make imprints of carbohydrate derivatives substituted with covalently, but reversibly bonded vinylphenyl boric acid groups, so-called boronate esters, which after polymerisation have permitted hydrolysis and binding of a new print molecule (G. Wulff, ACS Symp. Series, 308 (1986) 186). Decisive of the selectivity of the thus prepared polymers are correctly positioned binding boronate groups and a well-shaped cavity. The drawback of this system is that a complicated chemical synthesis is necessary.

Prearranged boronate groups have also been used for Faking imprints of glycoprotein ((Transferrin, M. Glad, O. Norrlöw, B. Sellergren, N. Siegbahn, K. Mosbach, J. Chromatogr., 347 (1985) 11) and bis-nucleotides O. Norrlöw, M. O. Månsson K. Mosbach. J. Chromatogr., 396 (1987) 374) on silica. In this context, use has been made of a mixture of non-covalently bonding organic silanes and boronate silane, which has been caused to interact with a print molecule before polymerisation on the surface. The effect of recognition seems mainly to depend on the fact that the boronate groups are correctly spaced from each other to be able to interact effectively with the print molecules. Transferrin has a total of four silica acid groups and bis-NAD has four riboses which form boronate esters.

It is also known to use, in affinity chromatography methods, adsorption material having specific ligands, but these are randomly localised on the sorbent and may therefore yield poor selectivity. Furthermore, there will be a large number of unused ligands, which is uneconomical from the industrial point of view.

Immobilised phenyl boric acid has been used to separate carbohydrate derivatives (H. L. Weith, J. L. Wiebers, P. T. Gilham, Biochemistry, 91 (1970) 4) and also to separate glycosylised hemoglobin and other glycoproteins (P. D. G. Dean, P. J. Brown, V. Bouriotis, U.S. Pat. No. 4,269,605 (1981).

For purification and analysis, especially of biological macromolecules, selectivity is most important. It is frequently necessary to distinguish a single component in a mixture of, maybe, several thousand components. The known adsorption materials are in most cases not sufficiently selective and cause non-specific binding, which may completely destroy the result of an analysis.

Modern biotechnical production and analysis as well as a large amount of medical diagnostics are based on selective binding. The methods known so far are also for these purposes not sufficiently selective and/or sufficiently simple to be economically useful on an industrial scale. Therefore there is a need of an adsorption material having very high selectivity and low non-specific binding, which may be prepared on a large scale and at low cost.

SUMMARY OF THE INVENTION

According to the invention, a selective adsorption material is provided, which is especially suitable for adsorption of biological macromolecules, and which is characterised In that it comprises immobilised ligands which have been localised to selectively adsorb a predetermined molecule by their first being bound to a print molecule which has then been removed after the immobilisation of the ligand.

The invention also comprises a process for preparing a selective adsorption material, especially suitable for adsorption of biological macromolecules, characterised in that a print molecule having at least two separate binding sites is bonded to the corresponding, at least two immobilisable ligands, that the ligands are immobilised, and that subsequently the print molecule is removed.

Finally the invention relates to the use of the selective adsorption material for purification or analysis, especially of biological macromolecules.

BRIEF DESCRIPTION OF THE DRAWINGS

The difference between a prior art adsorption material and the invention is schematically shown in the accompanying drawings in which:

FIG. 2 shows a sorbent according to the invention, with specifically localised, binding groups.

Figure 1:
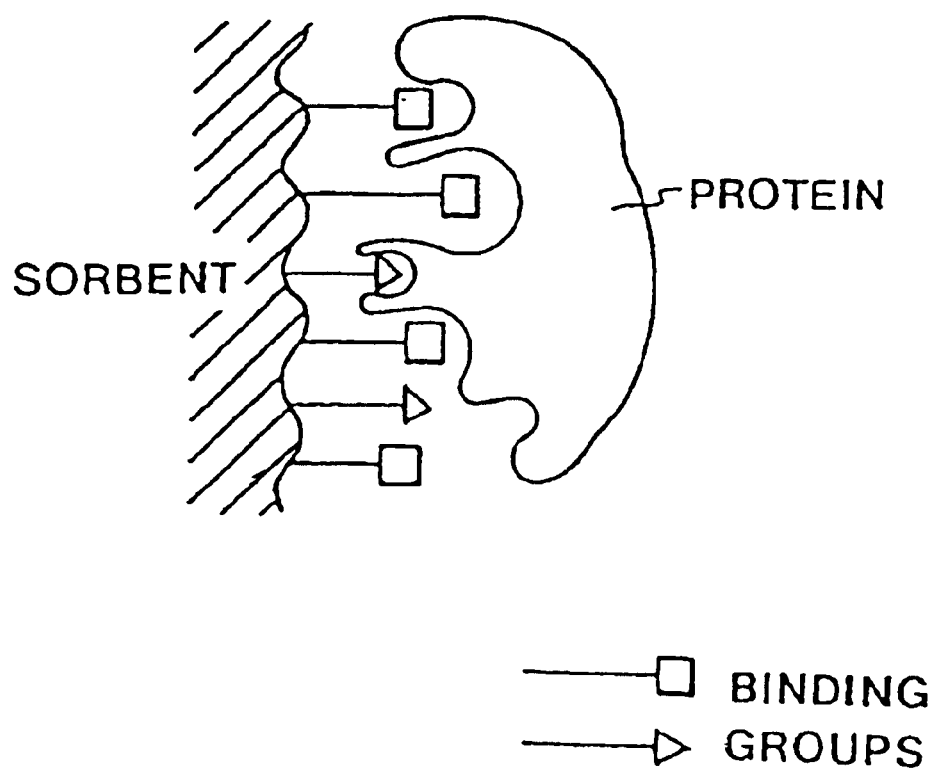
FIG. 1 is a schematic sketch of a prior art sorbent with randomly positioned binding groups, e.g., boronate, immobilised, metal.

After prebinding to the print molecule and the subsequent immobilisation, the binding groups (ligands) will be bonded preferably to the surface of a matrix. The correct localisation of ligands on two dimensions results in increased selectivity by the print molecule having at least two separate binding sites. The corresponding, at least two immobilised ligands will thus be correctly spaced apart. This results in optimal binding of the target molecule in the subsequent adsorption.

As is evident from that stated above, the invention thus relates to a form of directed immobilisation of affinity ligands or other (chemical) ligands. This directed immobilisation is achieved by means of a prebinding method. The advantage as compared to randomly immobilised binding groups is that the print molecule is bonded more effectively and with greater selectivity. At the same time, all ligands may be utilised, thereby avoiding an excess thereof, which otherwise may easily result in non-specific bonding which in turn results in a lower yield.

Ligands which are useful for the invention should carry groups that can be bonded to a print molecule, and groups which can be used for immobilisation of the ligands. One type of suitable ligand is a monomer which can be immobilised by polymerisation. Examples of groups that can be bonded to a print molecule are given In Table 1.

TABLE 1

| Group binding to print molecule on ligand/monomer | Binding group on print molecule |
|---|---|
| Imidazole-metal | Histidine, tryptophane, thiol |
| Iminodiacetic acid-metal | " |
| Carboxyl | Amine |
| Amine | Carboxyl |
| Carboxyl | Carboxyl, amide (hydrogen bonding) |
| Boronate | Carbohydrate, diol |
| Thiol | Thiol |
| Aldehyde | Amine |

Boronate, thiol and aldehyde are bonded covalently, whereas the other groups are bonded non-covalently to the print molecule.

Among groups that may be used for immobilisation, mention can be made of silanes which bind silanol and hydroxyl groups, and vinyl, acryl and methacryl which polymerise an a matrix.

Other ligands/monomers that may be used are:
Acryloyhistamine: H. Morawetz, W. R. Song, JACS, 88 (1966) 571.
Boronate silane: M. Glad, O. Norrlöw, B. Sellergren, N. Siegbahn, K. Mosbach, J. Chromatogr., 347 (1985) 11.
IDA-silane: A. Figueroa, C. Corradini, B. Felbush, B. L. Karger, P. Chromatogr., 371 (1986) 335.

Moreover, different types of ligands may be used simultaneously in one preparation. For example, use can be made of both boronate binding and metal interaction on the same print molecule if this is e.g. a glycoproten with surface-bound histidines.

As print molecule (imprinting molecule) for prearrangement of the ligands, the invention preferably uses biological macromolecules, e.g. enzymes, antibodies, glycoproteins or other proteins, nucleic acids, polysaccharides. The molecular imprinting is preferably carried out in aqueous media which are the normal surroundings of these molecules. It has also become apparent that larger or smaller amounts of organic solvents which are miscible with water, such as DMF (dimethylformaide), DMSO (dimethylsulforide), formamide (M. Ståhl, M. O. Månsson, K. Mosbach, Biotechn. Lett., 12 (1990) 161; N. Chang, S. J. Hen, A. M. Klibanov, BBRC, 176 (1991) 1462), may be added. In some cases, also pure DMSO can be used, in which protein and a monomer mixture (the ligands) are dissolved. A polymerised product is obtained, having a sufficient amount of correctly positioned, binding groups to provide a certain selectivity.

Matrix materials which are useful according to the invention must contain surface-bound reactive groups which can react with and covalently bind prearranged ligands. The matrices may be solid or in the form of gels and comprise particles, chips, electrodes, gel etc. Suitable matrix materials are silica (particles, chips etc.), glass (particles, electrodes etc.), biological polymers (agarose, dextran, gelatin etc.) and synthetic polymers (polyvinyl alcohol, TRIM (P. Reinholdsson, T. Hargitai, B. Törnell, R. Isaksson, Angew. Macromol. Chem., 1991, in press) etc.) When the matrix consists of a particulate solid phase, the surface is to be found both on the outside of the particles and on the surface of the pores thereof. In most cases, the latter surface is many times larger than the former.

Reactive groups on the matrix material can be acrylate, methacrylate. vinyl, hydroxyl or silanol.

If the matrix material contains no suitable reactive groups, it may be derivatised in advance with suitable groups, such as methacryl groups, before immobilising the ligands on the matrix.

The invention will now be described in more detail by means of the following, non-restrictive Example.

EXAMPLE

Methcrylate Silica 3-methacryloyloxypropyltrimethoxysilane (2.0 g, 8.1 mmol, Fluka) was mixed with 100 ml of water and dissolved during powerful stirring by means of a magnetic stirrer at 22° C. for 4 h. Porous silica (5.0 g, "Lichrospher Si 300", Merck) was suspended in 20 ml of water and treated with vacuum and ultrasonics, thereby producing pores free from air. Subsequently, the silane solution was added, and the silanisation was allowed to proceed for 4 h at 60° C. in a round-bottomed flask placed In a water bath and fitted with a TEFLON, tetrafluoroethylene fluorocarbon polymer, which is a trademark of Dupont Chemical Company—coated blade mixer. The derivatised silica was washed on a glass filter with water and methanol and then air-dried on the filter.

Titration with bromine water (according to Glad et al, J. Chromatogr., 347 (1985) 11) yielded 335 µmol of methacrylate groups per g of silica product. A carbon analysis yielded 620 µmol of silane per g of silica product, which indicates that more than half of the groups are still reactive to subsequent immobilisation.

Preparation

Mixtures according to the Table below with RNase B and STI (Soybean trypsine inhibitor), respectively, as print molecule.

|  | mg | µmol |
|---|---|---|
| Methacrylate-silica | 800 | 268 |
| Vinyl imidazole[1] | 0.39 | 4.14 |
| Acrylphenyl boric acid | 1.59 | 8.32 |
| Acrylamide | 100 | 1410 |
| PDA (piperazine diacrylamide) | 50 | 257 |
| TEMED (N,N,N',N'-tetramethylenediamine) | 5 |  |
| ZnCl$_2$ | 0.64 | 4.70 |
| Water/DMF (7/3, w/w) | 2.5 ml |  |
| Ammonium persulphate |  |  |
| alt. A) RNase B (molecular weight 14700) | 10 | 0.73 |
| alt. B) STI (molecular weight 20100) | 10 | 0.53 |

[1]ref. C. G. Overberger, N. Vorchheimer, JACS, 85 (1963) 951

After mixing the respective print molecule with all the other ingredients in a total of 2.5 ml of water/DMF, the samples were cooled, and then N$_2$ gas was conducted through the mixture. After about 30 s, the mixture began to solidify. The preparation was allowed to stand for 1 h, and subsequently the substituted silica particles were washed on a glass filter with water/DMF. Small polymer particles were removed by sedimentation, and the remaining particles were packed in steel columns (5×0.5 cm). When injecting RNase B on preparation A, the elution was delayed as compared with preparation B.

As an alternative to vinyl imidazole, vinyl benzyl iminodiacetic acid can be used (L. R. Morris, R. A. Mock, C. A. Marshall, J. H. Howe, JACS, 81 (1959) 377). These bind metal ions, e g. Zn$^{2+}$, and Cu$^{2+}$, which have been used for a long time in so-called immobilised metal affinity chromatography (J. Porath, J. Carlsson, I. Olsson, G. Belfrage, Nature. 258 (1975) 598).

What is claimed is:

1. A process for producing a molecularly imprinted adsorption material, comprising the steps of:

forming non-covalent or reversible-covalent bonds between at least two ligands and a protein print molecule, said at least two ligands becoming at least two bound ligands, each one of said at least two ligands comprising at least two different functional groups, having at least one of said at least two different functional groups being an imidazole-metal, an iminodiacetic acid-metal, a carboxyl, an amine, a thiol, or an aldehyde and which is reversibly bound to said print molecule;

immobilizing said at least two bound ligands to a matrix by covalently binding at least one of said at least two different functional groups to said matrix;

extracting said protein print molecule from said immobilized at least two bound ligands, said extracting of said protein print molecule forming a stereo-tailored zone;

producing a molecularly imprinted adsorption material.

2. The molecularly imprinted adsorption material produced by the process of claim 1, having said functional group comprising an imidazole-metal or an iminodiacetic acid-metal and said functional group being reversibly bound to a protein print molecule.

3. The molecularly imprinted adsorption material produced by the process of claim 1, in which said ligands are monomers and in which said immobilizing comprises a further step of polymerizing said monomers.

4. The molecularly imprinted adsorption material produced by the process of claim 1, having said stereo-tailored zone configured to an enzyme or glycoprotein.

5. The molecularly imprinted adsorption material produced by the process of claim 1, having said matrix formed through the polymerization of said different functional groups into a cross-linked polymer.

6. The process according to claim 1, further comprising the step of:

forming said matrix through the polymerization of said different functional groups into a cross-linked polymer.

7. The process according to claim 1, further comprising the step of:

binding at least one of said at least two different functional groups to an already existing matrix.

8. A molecularly imprinted adsorption material for adsorbing protein molecules comprising:

a matrix, at least two ligands covalently bound to the surface of said matrix by directed immobilization forming at least two immobilized ligands, in which each of said at least two ligands include at least two different functional groups, in which at least one of said at least two different functional groups is an imidazole-metal or an iminodiacetic acid-metal, a molecularly imprinted stereo-tailored zone.

9. The molecularly imprinted adsorption material of claim 8, having said matrix comprising a silica, a glass, or mixtures thereof.

10. The molecularly imprinted adsorption material of claim 8, having said matrix comprising a methacrylate-silica material.

11. The molecularly imprinted adsorption material of claim 8, having said matrix comprising an acrylate or a methacrylate surface bound reactive group.

12. The molecularly imprinted adsorption material of claim 8, having the adsorption material stereo-tailored to selectively adsorb a protein.

13. The molecularly imprinted adsorption material of claim 8, having the adsorption material stereo-tailored to selectively adsorb an enzyme.

14. The molecularly imprinted adsorption material as claimed in claim 8, having said matrix comprising a silica, a silane and a derivatized vinyl monomer.

15. The molecularly imprinted adsorption material of claim 8, having said matrix comprising a biological polymer, a synthetic polymer, or mixtures thereof.

16. The molecularly imprinted adsorption material of claim 8, having said matrix comprising a monomer.

17. The molecularly imprinted adsorption material of claim 8, having said matrix comprising a vinyl surface bound reactive group.

18. The molecularly imprinted adsorption material of claim 8, having said matrix comprising a hydroxyl surface bound reactive group.

19. The molecularly imprinted adsorption material of claim 8, having said matrix comprising a silanol surface-bound reactive group.

20. The molecularly imprinted adsorption material of claim 8, having the adsorption material stereo-tailored to selectively adsorb a nucleic acid.

21. The molecularly imprinted adsorption material of claim 8, having the adsorption material stereo-tailored to selectively adsorb a polysaccharide.

22. The molecularly imprinted adsorption material of claim 8, having the adsorption material stereo-tailored to selectively adsorb a glycoprotein.

* * * * *